(12) United States Patent
Hou

(10) Patent No.: US 10,371,613 B2
(45) Date of Patent: Aug. 6, 2019

(54) APPARATUS AND METHOD FOR LOADING AND WEAR TESTING A RUBBER SAMPLE

(71) Applicant: The Yokohama Rubber Co., LTD., Minato-ku, Tokyo (JP)

(72) Inventor: Gang Hou, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 127 days.

(21) Appl. No.: 15/512,049

(22) PCT Filed: Aug. 26, 2015

(86) PCT No.: PCT/JP2015/074068
§ 371 (c)(1),
(2) Date: Mar. 16, 2017

(87) PCT Pub. No.: WO2016/042998
PCT Pub. Date: Mar. 24, 2016

(65) Prior Publication Data
US 2017/0284915 A1    Oct. 5, 2017

(30) Foreign Application Priority Data

Sep. 16, 2014    (JP) ................................. 2014-187960

(51) Int. Cl.
*G06F 11/00*    (2006.01)
*G01N 33/36*    (2006.01)
(Continued)

(52) U.S. Cl.
CPC .............. *G01N 3/56* (2013.01); *G01N 33/36* (2013.01); *G01N 33/445* (2013.01);
(Continued)

(58) Field of Classification Search
CPC ........ G01N 3/56; G01N 33/36; G01N 33/445; G01N 3/00; G01N 33/00; G01N 2203/0266; G01N 2203/0294; G06F 11/006
(Continued)

(56) References Cited

U.S. PATENT DOCUMENTS 5,689,058 A * 11/1997 Yuan ........................ G01N 3/56
73/9
5,934,663 A * 8/1999 Saito ...................... B65H 27/00
198/780

(Continued)

FOREIGN PATENT DOCUMENTS

CN      200965503      10/2007
JP      S51-002990     1/1976
(Continued)

OTHER PUBLICATIONS

Translation KR-20090055460-A (Year: 2009).*
International Search Report for International Application No. PCT/JP2015/074068 dated Nov. 17, 2015, 4 pages.

*Primary Examiner* — Natalie Huls
*Assistant Examiner* — Monica S Young
(74) *Attorney, Agent, or Firm* — Thorpe North & Western

(57) ABSTRACT

A wear testing method includes setting a rotational speed of a rotary drum with a rubber sample attached to an outer surface thereof to a desired speed; setting a pressing load imparted by a contact member to a desired pressing load via a weight member; selecting as the contact member a desired contact member from a plurality of contact members with varying specifications for a contact surface that comes into contact with the surface of the rubber sample; attaching an arm portion that composes a pressing mechanism; rotating the rotary drum; and pressing the contact member against the surface of the rubber sample with the contact member (Continued)

being moveable in a tangent line direction of a rotation direction of the rotary drum, and detecting an amount of displacement in a pressing direction of the contact member pressing against the surface of the rubber sample via a displacement sensor.

7 Claims, 3 Drawing Sheets

(51) Int. Cl.
    *G01N 3/56*     (2006.01)
    *G01N 33/44*     (2006.01)
    *G01N 3/00*     (2006.01)
    *G01N 33/00*     (2006.01)

(52) U.S. Cl.
    CPC .............. *G06F 11/006* (2013.01); *G01N 3/00* (2013.01); *G01N 33/00* (2013.01); *G01N 2203/0266* (2013.01); *G01N 2203/0294* (2013.01)

(58) Field of Classification Search
    USPC ........................................................ 73/861.42
    See application file for complete search history.

(56) References Cited

U.S. PATENT DOCUMENTS

| | | | | |
|---|---|---|---|---|
| 5,987,961 | A | * | 11/1999 | Harris ...................... G01N 3/56 73/11.01 |
| 6,412,330 | B1 | * | 7/2002 | Dicello .................... G01N 3/56 73/7 |
| 2013/0036790 | A1 | * | 2/2013 | Hirayama ................ G01N 3/56 73/8 |

FOREIGN PATENT DOCUMENTS

| | | |
|---|---|---|
| JP | S52-132888 | 11/1977 |
| JP | H02-210243 | 8/1990 |
| JP | H06-028680 | 8/1994 |
| JP | 2001-088922 | 4/2001 |
| JP | 2007-218746 | 8/2007 |
| JP | 2013-036900 | 2/2013 |
| KR | 20090055460 A * | 6/2009 |

* cited by examiner

APPARATUS AND METHOD FOR LOADING AND WEAR TESTING A RUBBER SAMPLE

TECHNICAL FIELD

The present technology relates to a wear testing device and method, and particularly relates to a wear testing device and method capable of estimating with high accuracy wear resistance of an upper cover rubber of a conveyor belt should the conveyor belt actually be used.

BACKGROUND ART

Various objects, including mineral resources such as iron ore and limestone, are conveyed by a conveyor belt. When the objects are conveyed by the conveyor belt, the objects to be conveyed are fed onto an upper rubber cover of the conveyor belt from a hopper or another conveyor belt. The fed objects to be conveyed are carried on the upper rubber cover and conveyed in a traveling direction of the conveyor belt. When the objects to be conveyed are fed onto the upper rubber cover of the conveyor belt, the upper rubber cover is subject to impact, and when the surfaces of the objects to be conveyed are sharp, the upper rubber cover sometimes sustains cut damage. When the objects to be conveyed are loaded on the upper rubber cover and conveyed, the upper rubber cover is subject to wear as a result of the objects to be conveyed sliding on the upper rubber cover. Thus, in known art, various proposals have been made (see Japanese Unexamined Patent Application Publication No. 2001-88922A, for example) in order to improve wear resistance of the upper rubber cover.

The amount of wear, and the like occurring in the upper rubber cover significantly change depending on environment in which the conveyor belt is used (including the types of the objects to be conveyed). To estimate wear resistance of the upper cover rubber with high accuracy, evaluation is most preferably performed under conditions similar to the actual use environment. Accordingly, there is a demand for a testing device that performs evaluation to have condition settings that conform to the various environments in which the conveyor belt is used.

Examples of known testers that perform evaluation of wear resistance for rubber include a DIN (Deutschen Institut für Normung (German Institute for Standardization)) wear tester and a Williams wear tester. However, these wear testers have the object of obtaining wear resistance under certain preset conditions. Thus, they cannot be set for conditions that conform to various environments in which the conveyor belt is used and are inadequate in estimating with high accuracy wear resistance of the upper cover rubber of the conveyor belt should the conveyor belt actually be used.

SUMMARY

The present technology provides a wear testing device and method capable of estimating with high accuracy wear resistance of an upper cover rubber of a conveyor belt should the conveyor belt actually be used.

An embodiment of the present invention is a wear testing device comprising a rotary drum with variable rotational speed; a contact member able to be brought into contact with a surface of a rubber sample attached to an outer surface of the rotary drum; a pressing mechanism that presses the contact member against the surface of the rubber sample; a weight member that changes a pressing load imparted by the contact member; and a displacement sensor that detects an amount of displacement in a pressing direction of the contact member pressing against the surface of the rubber sample; the contact member being a plurality of contact members with varying specifications for a contact surface that comes into contact with the surface of the rubber sample; and a contact member that comes into contact with the surface of the rubber sample discretionarily selected from the plurality of contact members being able to be pressed against the surface of the rubber sample while being moveable in a tangent line direction of a rotation direction of the rotary drum.

Another embodiment of the present technology is a wear testing method for a rubber sample attached to an outer surface of a rotary drum with variable rotational speed in which a contact member is pressed against a surface of the rubber sample by a pressing mechanism, the method comprising the steps of setting a rotational speed of the rotary drum to a desired speed;

setting a pressing load imparted by the contact member to a desired pressing load via a weight member; selecting as the contact member a desired contact member from a plurality of contact members with varying specifications for a contact surface that comes into contact with the surface of the rubber sample; and pressing the selected contact member against the surface of the rubber sample with the selected contact member being moveable in a tangent line direction of a rotation direction of the rotary drum, and detecting an amount of displacement in a pressing direction of the contact member pressing against the surface of the rubber sample via a displacement sensor.

According to the present technology, the rotational speed of the rotary drum and the pressing load imparted by the contact member can be set as desired. Additionally, the contact member having a contact surface with desired specifications can be pressed against the surface of the rubber sample. Here, the contact member can be pressed against the surface of the rubber sample while being moveable in the tangent line direction of the rotation direction of the rotary drum. As a result, when testing for wear resistance of rubber samples with the same specifications as rubber used in the upper cover rubber of a conveyor belt, evaluation can be performed under conditions that imitate actual use environments of the conveyor belt. Thus, wear resistance of the upper cover rubber of the conveyor belt should the conveyor belt actually be used can be estimated with high accuracy.

Additionally, by the amount of displacement in the pressing direction of the contact member pressing against the surface of the rubber sample being detected by the displacement sensor, the relationship not just between the pressing load and the amount of wear, but the relationship between the amount of compressive deformation and the amount of wear of the rubber sample can be obtained. In other words, the relationship between the state of deformation and the amount of wear of the rubber sample can be obtained.

The wear testing device according an embodiment of the present technology can further comprise a load sensor that successively detects the pressing load and a load in the tangent line direction of the rotation direction of the rotary drum acting on the contact member. This configuration enables the coefficient of dynamic friction of the rubber sample R to be obtained.

A casing can be further provided that can change an external environment temperature of the rubber sample. This configuration enables the external environmental temperature of the rubber sample to be set to a desired temperature.

As a result, evaluation can be performed in conditions that further imitate actual use environments of the conveyor belt.

A temperature sensor can be further provided that detects a surface temperature of the rubber sample. This configuration enables changes in surface temperature of the rubber sample during evaluation to be measured, and thus energy generated when the rubber sample wears to be measured.

The pressing mechanism described above can include an arm portion to which the contact member is attached, the arm portion being pivotally supported by a rotation shaft at a second end portion in a longitudinal direction in a manner such that when the arm portion is pressed by the weight member, the arm portion can pivot in a vertical direction about the rotation shaft.

DETAILED DESCRIPTION

Figure 1:
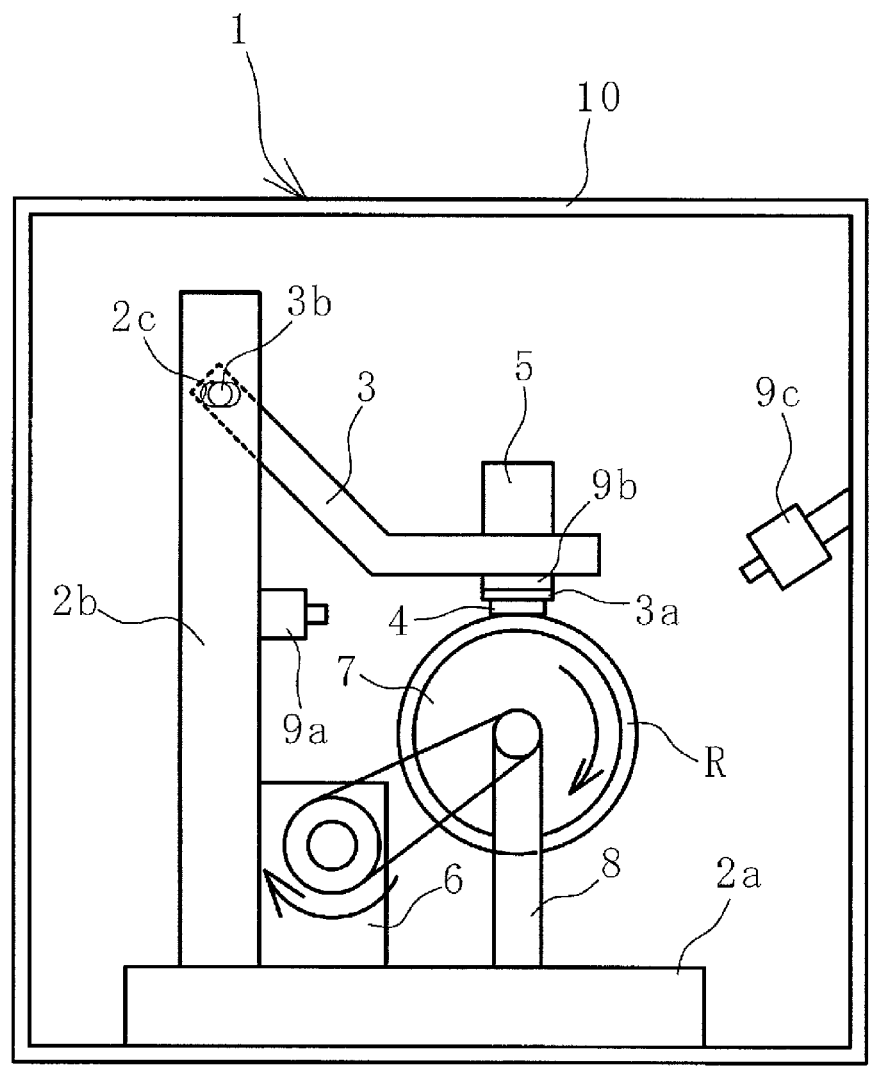
FIG. 1 is an explanatory diagram illustrating, in a front view, a wear testing device according to an embodiment of the present technology.
Figure 1:
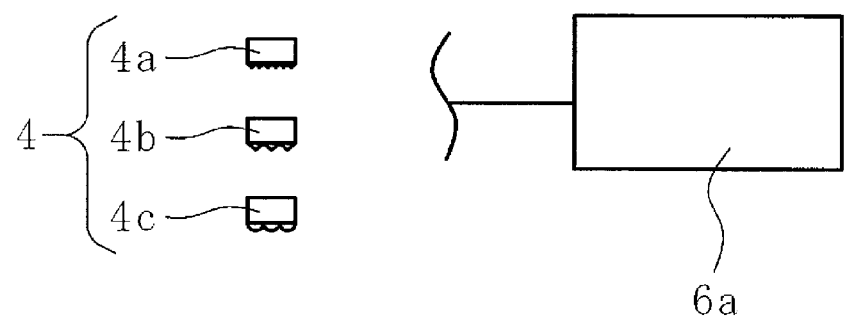

A wear testing device and method of embodiments of the present technology will be described below with reference to embodiments illustrated in the drawings.

Figure 3:
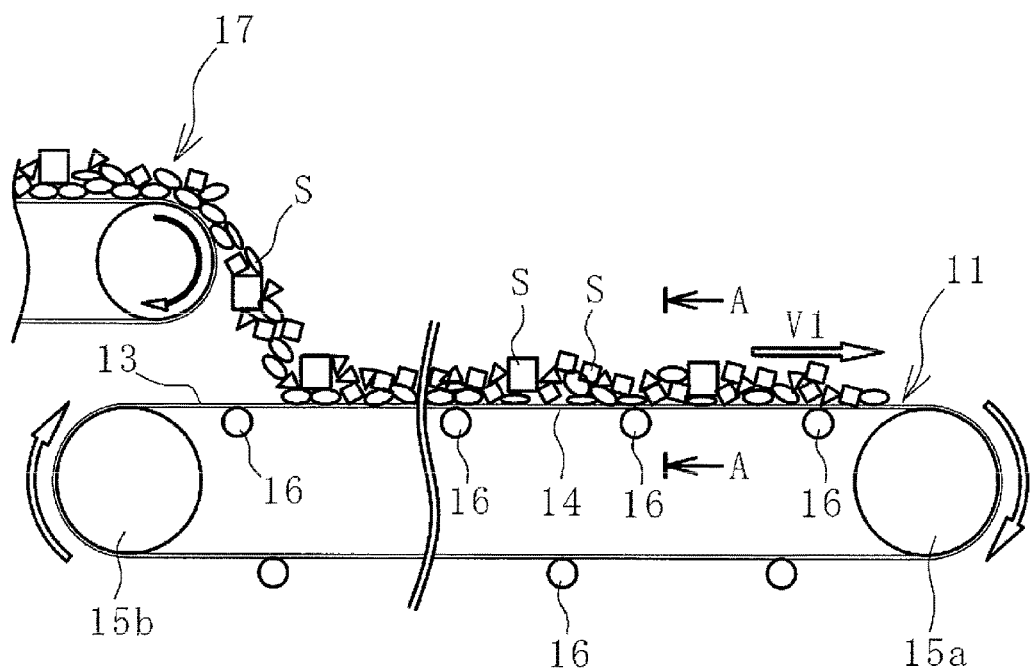
FIG. 3 is an explanatory diagram illustrating a conveyor belt line in a simplified manner.
Figure 4:
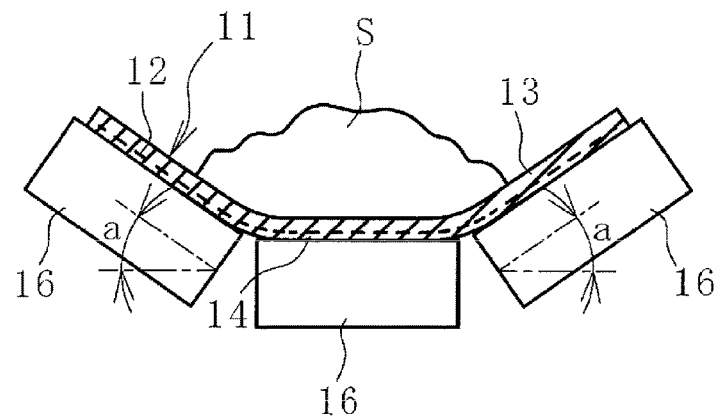
FIG. 4 is a cross-sectional view taken along A-A of FIG. 3.

In a functioning conveyor belt line, as illustrated in FIGS. 3 and 4, objects to be conveyed S conveyed by another conveyor belt 17 is fed onto a conveyor belt 11 and conveyed to a conveying destination by the conveyor belt 11. The objects to be conveyed S may be fed onto the conveyor belt 11 by a hopper and the like. The conveyor belt 11 is mounted between pulleys 15a and 15b at a prescribed tension.

The conveyor belt 11 is constituted by a core layer 12 including a core made of canvas, steel cord, or the like, and an upper cover rubber 13 and a lower cover rubber 14 that sandwich the core layer 12 therebetween. The core layer 12 is a member that bears the tension that causes the conveyor belt 11 to be stretched. The lower rubber cover 14 is supported by support rollers 16 on a carrier side of the conveyor belt 11, and the upper rubber cover 13 is supported by support rollers 16 on a return side of the conveyor belt 11. Three of the support rollers 16 are arranged on the carrier side of the conveyor belt 11 in the belt width direction. The conveyor belt 11 is supported by these support rollers 16 in a concave shape having a prescribed trough angle a. When the pulley 15a on a drive side is driven in rotation, the conveyor belt 11 is operated in one direction at a prescribed travel speed V1. The objects to be conveyed S are fed onto the upper rubber cover 13, and are loaded on the upper rubber cover 13 and conveyed.

Figure 2:
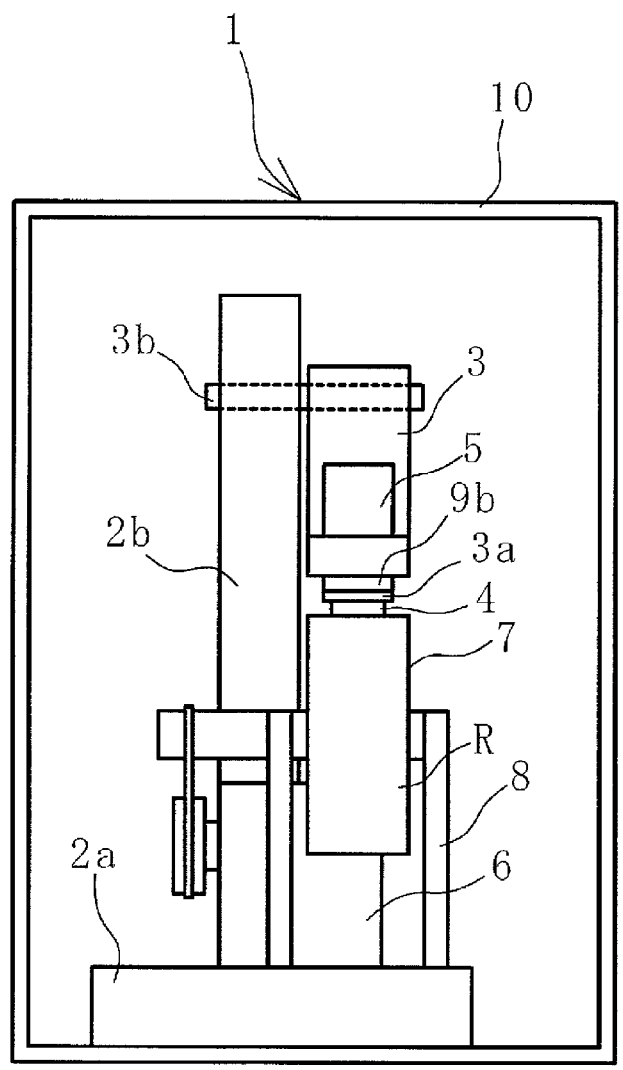
FIG. 2 is an explanatory diagram illustrating, in a side view, the wear testing device of FIG. 1.

A wear testing device 1 of an embodiment of the present technology illustrated in FIGS. 1 and 2 is provided with a rotary drum 7, a contact member 4, an arm portion 3 to which the contact member 4 is detachably attached, a weight member 5 detachably attached to the arm portion 3, a control unit 6a, and a displacement sensor 9a. The wear testing device 1 of this embodiment is further provided with a load sensor 9b, a temperature sensor 9c, and a casing 10 that houses all of the components described above except for the control unit 6a.

The casing 10 is capable of setting and maintaining the interior space at a desired temperature. In addition to temperature, the casing 10 is capable of setting and maintaining the interior space at a desired humidity.

The rotary drum 7 is supported for rotation by a support stand 8 that is fixed to a base 2a in an upright position. The rotary drum 7 is driven in rotation by a drive motor 6 via a transmission belt. The rotational speed of the rotary drum 7 is variable and can be set to a desired rotational speed. The rotational speed is controlled by the control unit 6a. The rotary drum 7 and the drive motor 6 can have a configuration in which driving force is transmitted via a different mechanism such as a gear system.

A rubber sample R is attached to the outer surface of the rotary drum 7. In this embodiment, the rubber sample R is provided around the entire circumference of the outer surface of the rotary drum 7 to form an annular shape.

The arm portion 3 is fixed to a post 2b that is fixed to the base 2a in an upright position by being supported by a rotation shaft 3b allowing for pivoting in the vertical direction. The weight member 5 is attached to a first end portion of the arm portion 3 in the longitudinal direction. A second end portion of the arm portion 3 in the longitudinal direction is pivotally supported by the rotation shaft 3b that passes through a support slot 2c formed in the post 2b extending in the horizontal direction. This allows the arm portion 3 to be moveable in the horizontal direction to a certain degree. The arm portion 3 is provided with a pressing mechanism that presses the contact member 4 described below against the surface of the rubber sample R.

The contact member 4 is attached to the arm portion 3 at a position where contact with the surface of the rubber sample R is possible. Specifically, the contact member 4 is detachably attached to a holding portion 3a that is fixed to the first end portion of the arm portion 3 in the longitudinal direction.

The contact member 4 is a plurality of contact members 4 of which the surfaces that comes into contact with the surface of the rubber sample R has varying specifications (in terms of shape, hardness, material, surface roughness, and the like). In other words, the contact members 4 (4a, 4b, 4c) are each provided with a contact surface with specifications that imitates the surface of the objects to be conveyed S that are conveyed on the conveyor belt 11 that uses an upper cover rubber 13 of the same specifications of the rubber sample R.

For example, depending on whether the objects to be conveyed S are iron ore, limestone, or gravel, the sharpness, hardness, and the like differs. Accordingly, the plurality of contact members 4 have contact surfaces that imitate these conditions. A discretionary contact member 4 can be selected from the plurality of contact members 4 (4a, 4b, 4c) and attached to the holding portion 3a.

The weight member 5 is a plurality of weight members 5 of varying weight which are detachably attached to the first end portion of the arm portion 3 in the longitudinal direction. When the weight member 5 presses against the first end portion of the arm portion 3 in the longitudinal direction, the arm portion 3 pivots in the vertical direction about the rotation shaft 3b located at the second end portion of the arm portion 3 in the longitudinal direction. This causes the contact member 4 to press against the surface of the rubber sample R. The arm portion 3 of this embodiment has such a pressing mechanism. However, any pressing mechanism that can press the contact member 4 against the surface of the rubber sample R may be employed.

The weight member 5 is only required to be able to change the pressing load imparted by the contact member 4 against the rubber sample R. In other words, by changing the weight of the weight member 5, the pressing force of the contact member 4 against the surface of the rubber sample R can be changed.

The displacement sensor 9a is attached to the post 2b and detects the amount of displacement in the pressing direction of the contact member 4, which presses against the surface of the rubber sample R. In other words, the amount of vertical displacement of the contact member 4 is successively detected to detect the state of deformation of the rubber sample R being pressed.

The load sensor 9b is attached to the lower surface of the first end portion of the arm portion 3 in the longitudinal direction. The load sensor 9b successively detects the pressing load and the load in the tangent line direction of the rotation direction of the rotary drum 7 acting on the contact member 4. In other words, the load sensor 9b detects the load in the vertical direction and the load in the horizontal direction acting on the contact member 4 pressing against the rubber sample R.

The temperature sensor 9c successively detects the surface temperature of the rubber sample R. The detection data from the displacement sensor 9a, the load sensor 9b, and the temperature sensor 9c are inputted into the control unit 6a.

Next, a testing method for evaluating wear resistance of the rubber sample R using the wear testing device 1 will be described.

The rubber sample R, which is the evaluation object, is attached to the outer surface of the rotary drum 7, and the drive motor 6 is driven in rotation. The rotational speed of the rotary drum 7 is set to a desired speed, and the pressing load of the contact member 4 against the surface of the rubber sample R via the pressing mechanism is set to a desired pressing load via the weight member 5.

The desired contact member 4 is selected from the plurality of contact members 4 (4a, 4b, 4c) and installed on the holding portion 3a. By this, the desired contact member 4 presses against the surface of the rubber sample R, and the amount of displacement in the pressing direction of the contact member 4 pressing against the surface of the rubber sample R is detected by the displacement sensor 9a. In this embodiment, the contact member 4 presses against the surface of the rubber sample R at a position directly above the rotary drum 7 (axis of center of rotation).

The arm portion 3 is freely moveable in the horizontal direction to a certain degree. Thus, the contact member 4 presses against the surface of the rubber sample R while being moveable in the tangent line direction of the rotation direction of the rotary drum 7 (horizontal direction). By having the contact member 4 be moveable to a certain degree in the tangent line direction of the rotation direction of the rotary drum 7, an actual state of the objects to be conveyed S being fed on the upper cover rubber 13 of the conveyor belt 11 can be more realistically imitated. In such a manner, continuous pressing by the contact member 4 at a prescribed pressing load and rotation causes the rubber sample R to wear.

According to an embodiment of the present technology, evaluation can be performed under conditions that imitate actual use environments of the conveyor belt 11 that uses the upper cover rubber 13 of the same specification as the rubber sample R, which is the evaluation object. In other words, the rotational speed of the rotary drum 7 is set to be equivalent to the relative speed in the horizontal direction of the objects to be conveyed S fed onto the conveyor belt 11, in other words the difference between the speed in the horizontal direction of the objects to be conveyed S when actually fed onto the conveyor belt 11 and the travel speed in the horizontal direction of the conveyor belt 11. The pressing load imparted by the contact member 4 is set to be equivalent to the pressing load the objects to be conveyed S impart on the upper cover rubber 13 in accordance with the feed weight and the feed height per unit time of the objects to be conveyed S.

This enables the conditions to imitate the actual use environments of the conveyor belt 11. Thus, wear resistance of the upper cover rubber 13 of the conveyor belt 11 should the conveyor belt 11 actually be used can be estimated with high accuracy.

Additionally, by the amount of displacement in the pressing direction of the contact member 4 pressing against the surface of the rubber sample R being detected by the displacement sensor 9a, the relationship not just between the pressing load and the amount of wear, but the relationship between the amount of compressive deformation and the amount of wear of the rubber sample R can be obtained. In other words, the relationship between the state of deformation and the amount of wear of the rubber sample R can be obtained.

In this embodiment, the pressing load (in other words, the load in the vertical direction) and the load in the tangent line direction of the rotation direction of the rotary drum 7 (in other words, load in the horizontal direction) acting on the contact member 4 are successively detected. This enables the coefficient of dynamic friction of the rubber sample R to be obtained on the basis of the detection data.

Additionally, in this embodiment, the external environmental temperature of the rubber sample R can be set to a desired temperature via the casing 10. This enables evaluation to be performed in conditions that further imitate actual use environments of the conveyor belt 11. By performing evaluation at varying external environment temperatures, temperature dependency of wear resistance for the rubber sample R can be obtained.

Furthermore, the temperature sensor 9c allows changes in surface temperature of the rubber sample R to be measured during evaluation. As the rubber sample R wears, thermal energy is generated. Thus, the amount of energy involved in wear can be obtained from the results of temperature measurements via the temperature sensor 9c. The amount of energy varies depending on the type of rubber. Thus, the results of temperature measurement can be advantageously used in selecting a rubber that generates relatively less thermal energy.

The invention claimed is:

1. An apparatus for loading and wear testing a rubber sample, comprising:
    a rotary drum with variable rotational speed;
    a contact member able to be brought into contact with a surface of the rubber sample attached to an outer surface of the rotary drum;
    a pressing mechanism that presses the contact member against the surface of the rubber sample;
    a weight member that changes a pressing load imparted by the contact member; and
    a displacement sensor that detects an amount of displacement in a pressing direction of the contact member pressing against the surface of the rubber sample;

the contact member including a plurality of contact members with varying specifications for a contact surface that comes into contact with the surface of the rubber sample; and a contact member that comes into contact with the surface of the rubber sample discretionarily selected from the plurality of contact members being able to be pressed against the surface of the rubber sample while being moveable in a tangent line direction of a rotation direction of the rotary drum, the tangent line direction being perpendicular to the pressing direction of the contact member and perpendicular to an axial direction of the rotary drum;

wherein the pressing mechanism includes an arm portion to which the contact member is attached, the arm portion being pivotally supported by a rotation shaft that passes through a support slot extending in a same direction as the tangent line direction at a second end portion in a longitudinal direction.

2. The apparatus for loading and wear testing the rubber sample according to claim 1, further comprising a load sensor that successively detects the pressing load and a load in the tangent line direction of the rotation direction of the rotary drum acting on the contact member.

3. The apparatus for loading and wear testing the rubber sample according to claim 2, further comprising a casing that can change an external environment temperature of the rubber sample.

4. The apparatus for loading and wear testing the rubber sample according to claim 3, further comprising a temperature sensor that detects a surface temperature of the rubber sample.

5. The apparatus for loading and wear testing the rubber sample according to claim 1, further comprising a casing that can change an external environment temperature of the rubber sample.

6. The apparatus for loading and wear testing the rubber sample according to claim 1, further comprising a temperature sensor that detects a surface temperature of the rubber sample.

7. A wear testing method for a rubber sample attached to an outer surface of a rotary drum with variable rotational speed in which a contact member is pressed against a surface of the rubber sample by a pressing mechanism, the method comprising the steps of:

setting a rotational speed of the rotary drum to a desired speed;

setting a pressing load imparted by the contact member to a desired pressing load via a weight member;

selecting as the contact member a desired contact member from a plurality of contact members with varying specifications for a contact surface that comes into contact with the surface of the rubber sample; and pressing the selected contact member against the surface of the rubber sample with the selected contact member being moveable in a tangent line direction of a rotation direction of the rotary drum, and detecting an amount of displacement in a pressing direction of the contact member pressing against the surface of the rubber sample via a displacement sensor, the tangent line direction being perpendicular to the pressing direction of the contact member and perpendicular to an axial direction of the rotary drum;

wherein the pressing mechanism includes an arm portion to which the contact member is attached, the arm portion being pivotally supported by a rotation shaft that passes through a support slot extending in a same direction as the tangent line direction at a second end portion in a longitudinal direction.

\* \* \* \* \*